United States Patent [19]

Jenkins et al.

[11] 3,997,297

[45] Dec. 14, 1976

[54] METHOD AND APPARATUS FOR DETECTING A CONSTITUENT IN AN ATMOSPHERE

[76] Inventors: Anthony Jenkins, 54 Finchams Close, Linton, Cambridgeshire; Douglas Walter Isgrove, 144 Malvern Road, Cherryhinton, Cambridgeshire, both of England

[22] Filed: Mar. 27, 1975

[21] Appl. No.: 562,681

[52] U.S. Cl. .......................... 23/232 E; 23/254 E; 73/23
[51] Int. Cl.² ................ G01N 27/30; G01N 27/64; G01N 33/22
[58] Field of Search ........ 23/254 R, 254 E, 255 R, 23/255 E, 232 R, 232 E; 73/23, 26

[56] References Cited

UNITED STATES PATENTS

| | | | |
|---|---|---|---|
| 2,449,067 | 9/1948 | Guillemin, Jr. | 23/254 X |
| 3,046,098 | 7/1962 | Brasseur et al. | 23/254 R |
| 3,425,807 | 2/1969 | Levy | 23/254 R |
| 3,753,653 | 8/1973 | Brieva et al. | 23/254 X |
| 3,883,739 | 5/1975 | Jenkins | 23/254 E |
| 3,909,204 | 9/1975 | Allen | 23/254 E |

*Primary Examiner*—R.E. Serwin
*Attorney, Agent, or Firm*—Woodhams, Blanchard and Flynn

[57] ABSTRACT

A method and apparatus for detecting the presence of a particular constituent in a sampled atmosphere. The sample is drawn through two substantially identical flow paths, each path containing a detector. The conditions prevailing in one of the flow paths is such as to convert the particular constituent into matter which will not produce a response in the associated detector. When the particular constituent is vapor originating from an explosive the conversion can be by heating the flow path to a temperature at which the vapor breaks down into components which do not produce a response in the associated detector. In the absence of the particular constituent in the sampled atmosphere the signals from the two detectors are substantially equal but the presence of the particular constituent results in a difference in signals from the two detectors.

12 Claims, 2 Drawing Figures

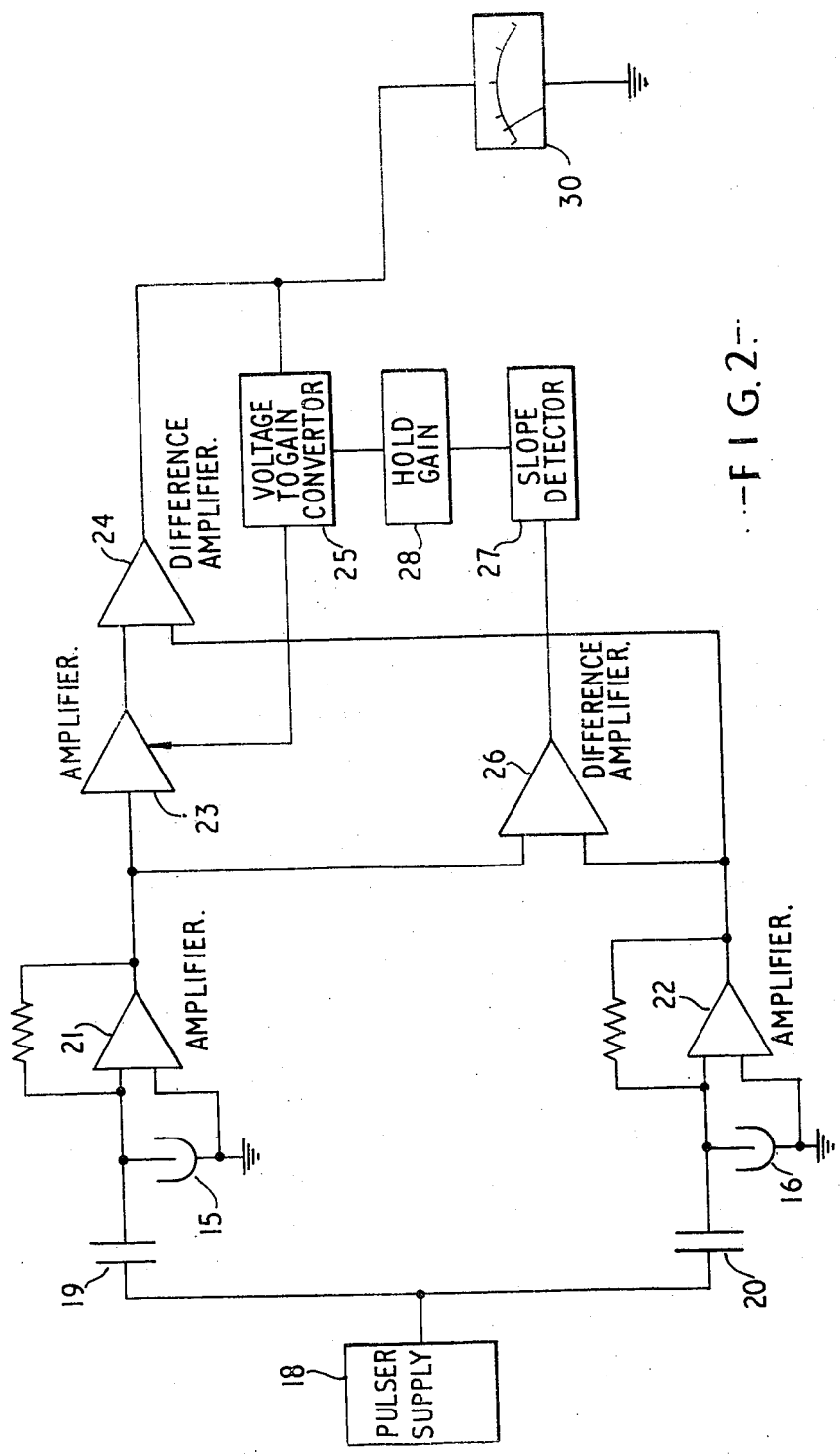

METHOD AND APPARATUS FOR DETECTING A CONSTITUENT IN AN ATMOSPHERE

The present invention concerns a method and apparatus for detecting the presence of a particular constituent in an atmosphere.

In order to positively detect a particular constituent in an atmosphere it is required to ensure that any detector system will respond to the presence of the constituent and will not be sensitive to the presence of other constituents which might produce signals which could mask the required signal. Where a detector system is responsive to more than one possible atmospheric constituent difficulty can arise in relating any resulting signal to a particular constituent. The present invention seeks to provide a method and apparatus that can identify a particular constituent of interest in an atmosphere. The invention is capable of detecting vapours emitted from nitro-compounds present in explosives. By virtue of the invention, such vapours can be detected by an electron capture detector even though such a detector is also sensitive to other components which might be present in the atmosphere, for example components such as halogenated hydrocarbons.

According to one aspect of the present invention a method of detecting the presence of a particular component in an atmosphere comprises drawing a sample of the atmosphere along two substantially identical flow paths, each path containing a detector, and converting the particular constituent content in one of said paths into matter incapable of producing a response in the associated detector whereby in the absence of said particular constituent in the atmosphere no significant difference is detectable between the signals emitted by the two detectors as the flows along the two paths into the detectors are substantially identical but in the presence of said particular constituent the flow content along said one path is altered to change the signal from the associated detector and the resultant difference in signals from the two detectors is indicative of the presence of the particular constituent in the sampled atmosphere.

According to another aspect of the present invention an apparatus for detecting the presence of a particular constituent in an atmosphere comprises first and second substantially identical flow paths, each path containing a detector, and means associated with one path only capable of converting the particular constituent content in said one path into matter incapable of producing a response in the associated detector whereby in the absence of said particular constituent in the sampled atmosphere no significant difference is detectable between the signals emitted by the two detectors but in the presence of said particular constituent the resultant difference in signals from the two detectors is indicative of the presence of said particular constituent in the sampled atmosphere.

The invention will be further described with reference to the accompanying schematic drawings; in which:

FIG. 2 is a diagrammatic electrical circuit of the arrangement in FIG. 1.

Figure 1:
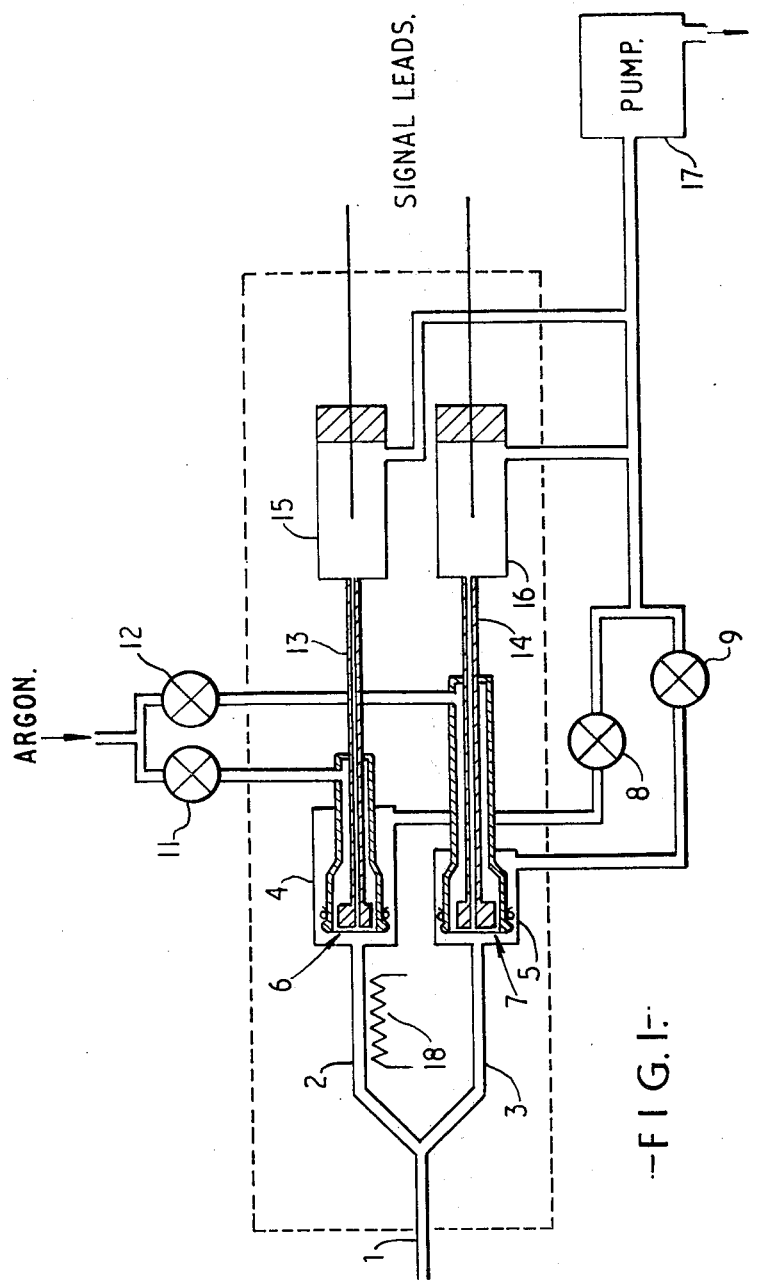
FIG. 1 is a diagrammatic arrangement of an embodiment of the invention.

With reference to FIG. 1, an atmosphere, such as air, to be sampled is drawn through a probe or nozzle 1 by means of a suction pump 17. The portion of the apparatus in FIG. 1 within the rectangular dotted outline is maintained at an elevated temperaturre which can be from 100° to 150° C. The temperature can be regulated by heater means controlled by thermostats. This is to prevent or minimise the possibility of the trace materials which are to be detected from adhering to the walls of the flow paths.

The incoming air flow divides into two streams and flows along long tubes 2 and 3 made of chemically inert material. One of the tubes, the tube 2, is heated, for example by an electrical heater 18, to a temperature which will break down any organic nitro-compounds present in the flow into products which are not electron capturing. The temperature of the tube 2 is not so high as to cause breakdown of the more stable halocarbon molecules which might be present in the sampled atmosphere.

Upon leaving the tubes 2 and 3 both streams impinge on identical, selectively permeable membranes 6 and 7. The membranes can be silastomer membranes. Heavy organic vapours can pass readily through the membranes but the remaining constituents of the air, including oxygen which is an electron absorber and is capable of producing a response in an electron capture detector, cannot or are less readily able to pass through the membranes. The air flows along the tubes 2 and 3 and over the membranes 6 and 7 are maintained substantially identical by means of control valves 8 and 9 in the flows leading to the pump 17. The vapours passing through the membranes are swept by a carrier gas flow, conveniently Argon, through respective tubes or columns 13 and 14 into electron capture detectors 15 and 16. The detectors 15 and 16 both exhaust the pump 17 and the Argon flows in the respective flow paths are regulated by selectively adjustable valves 11 and 12.

Briefly, an electron capture detector is an ionisation cell having a pair of spaced apart electrodes and a source of ionising radiation, for example, tritium or $Ni_{63}$, therein. A carrier gas on flowing through the detector is ionised by emission from the source. By applying a voltage between the electrodes, and conveniently the voltage is pulsed, the free electrodes formed by the ionising emission are collected at the anode to provide a detector standing current. If a trace of material containing molecules which are electron absorbing (the electron capture material) is introduced into the carrier gas flowing through the detector some of the free electrons will be captured by these molecules. The result is detectable by a change in the standing current.

In FIG. 1, the heater 18 is shown positioned upstream of the membrane 6 to heat the tube 2. Alternatively, it is possible to locate the heater, or other means to raise the temperature to a level at which nitro-compounds break down, downstream of the membrane 6. Thus, the heating can be applied to the tube 13 leading to the detector 15. As the flow along the tube 13 is substantially free of oxygen due to the difficulty of oxygen in traversing the membrane the application of the heater to the tube 13 will minimise any oxidation of the flow to the detector.

In use, an atmosphere being sampled is divided equally into two streams. When the atmosphere contains a halogenated hydrocarbon, which might be a trace of a pesticide, although the stream flowing through the tube 2 is heated to a higher temperature than that flowing through the tube 3 it suffers no degradation of its halocarbon content. The halocarbon contents of the two streams then pass through the respective membranes 6 and 7 and the halocarbons are carried by the carrier gas into the detectors. The detectors 15 and 16 even when of identical geometry and identical operating characteristics may give unequal responses and if the detector signal outputs are subtracted by a difference amplifier a small signal could appear at the output of the difference amplifier when the atmosphere contains a halogenated hydrocarbon. However when the atmosphere being sampled contains an organic nitro-compound, for example the vapours from explosives, the nitro-compound in the flow through the tube 2 is broken down whereas the flow through the tube 3 remains undisturbed. Consequently no detectable flow of nitro-compound enters the detector 15 whereas the nitro-compound flowing through tube 3 enters the detector 16. In this case, and assuming that no other detectable components such as halogenated hydrocarbons are present in the atmosphere being sampled no signal is obtained from the detector 15 and the difference signal from the amplifier previously mentioned is equal to the signal obtained from the detector 16.

Alternatively if a halogenated hydrocarbon is present in the atmosphere in addition to the nitro compound then both detectors will emit signals but the signals will not be equal and will provide a resultant difference signal.

In order therefore to distinguish between the presence of such components as halogenated hydrocarbons on the one hand and vapours emitted by nitro-compounds on the other hand it is required to arrange that the difference signal is zero for halogenated hydrocarbons and the like and that a detectable difference signal is obtained in the presence of the vapours from the nitro-compounds. It would be possible to trim the gain of two pre-amplifiers connected to each detector so that the difference of the two outputs resulting from sampling a halogenated atmosphere was zero. However, because of drift of the ion current which can be caused by varying contaminating levels, deposition in the detector and polarisation of the detector, the response to halogen may vary over comparatively short periods and would necessitate readjustment of the gain at regular intervals.

FIG. 2 shows a circuit which eliminates the necessity of manually adjusting the gain of the pre-amplifiers.

In FIG. 2, both detectors 15 and 16 are supplied by the same pulsed polarising supply 18 through low leakage capacitors 19 and 20. The pulsed voltage can be 60 volt high for a duration of 1 $\mu s$ at a frequency of 50 kHz. The detector outputs are connected to two similar current amplifiers 21 and 22. The gain of amplifier 21 may be less than that of the amplifier 22. The output from amplifier 21 is fed into a boost amplifier 23 whose gain is controlled by an output to gain converter 25. The output from the amplifier 23 is fed together with the output from the amplifier 22 into a difference amplifier 24. The output from the difference amplifier is fed to a display device such as a meter 30.

The converter 25 adjusts the gain of the amplifier 23 until no signal appears at its input, i.e. the output of the difference amplifier 24. In this way the amplification applied to signals from the detector 15 is adjusted automatically so that the output is zero at all times. The only way to obtain an output signal is to freeze the gain which is controlled by the converter 25 so that a difference signal can be observed. This must be performed when a rapid change occurs in the output of one detector only such as when a response is obtained from the presence of a nitro compound. This condition is detected by a second difference amplifier 26 whose inputs are connected to the outputs of the two current amplifiers 21 and 22. The output of the amplifier 26 is connected to a slope detector 27 which actuates a "hold gain" circuit 28 when rapid changes occur in the difference between the two detector currents. The slope detector functions by detecting a required rate of change of the output from the amplifier 26, the rate of change produced by the presence of a nitro-compound having been previously established.

The gain is held at the value which had just previously been sufficient to maintain the two amplified signals equal. The signal from the responding detector is thus passed to the display device. The "hold" circuit can be released in a number of ways, for example, on the reverse slope of the responding peak or by a simple timer circuit or when the output signal from the difference amplifier again approaches zero.

Whilst the above is particularly concerned with the detection of explosives by "sniffing" the atmosphere for vapours emitted by explosives, it will be appreciated that the invention is not confined to such use. Certain drugs emit characteristic vapours and the invention can also be employed in the detection of such drugs. Whilst the electron capture detector is particularly sensitive to the presence of nitro-compounds such as originating from explosives, in other applications it might be desirable to employ alternative forms of detector, for example a flame ionisation detector.

We claim:
1. A method of detecting the presence of a particular constituent in an atmosphere which comprises drawing a sample of the atmosphere along two substantially identical flow paths, each path containing a respective detector capable of detecting said particular constituent, and converting said particular constituent content in one but not the other of said flow paths into matter incapable of producing a response in the associated detector, and passing the flows in said paths to the respective detectors, whereby in the absence of said particular constituent in the atmosphere no significant difference is detectable between the signals emitted by the two detectors as the flows along the two paths into the detectors are substantially identical but in the presence of said particular constituent the flow content along said one path is altered to change the signal from the associated detector and the resultant difference in signals from the two detectors is indicative of the presence of the particular constituent in the sampled atmosphere.

2. A method of detecting vapours emitted by explosives in an atmosphere which comprises drawing a sample of the atmosphere along two substantially identical flow paths as two respective and substantially identical flows, each path containing a respective electron capture detector, and upstream of the corresponding detector converting the explosives vapours content in one but not the other of said paths into components which are non-electron capturing, and in the absence of said vapours in the atmosphere causing said detectors to emit signals between which no significant difference is detectable with the flows along the two paths into the detectors being substantially identical, but upon addition of said vapours to said atmosphere permitting the flow content to the detector in said other path to change the signal therefrom, and employing the resultant difference in signals from the two detectors to indicate the presence of vapours emitted by explosives in the atmosphere.

3. A method according to claim 2 which comprises maintaining a temperature differential between the two flow paths with said one path being at a higher temperature and therewith causing break-down of the explosives vapours in said one flow path into non-electron capturing components.

4. An apparatus for detecting the presence of a particular constituent in an atmosphere which comprises first and second substantially identical flow paths for receiving sampled atmosphere, each path containing a respective detector, and means associated with one path but not the other for converting the particular constituent content in said one path into matter incapable of producing a response in the associated detector, whereby in the absence of said particular constituent in the sampled atmosphere no significant difference is detectable between the signals emitted by the two detectors but in the presence of said particular constituent the resultant difference in signals from the two dectectors is indicative of the presence of said particular constituent in the sampled atmosphere.

5. An apparaus for detecting vapours emitted by explosives comprising first and second substantially identical flow paths for receiving sampled atmosphere, each path containing a respective electron capture detector, means associated with only one path and upstream from the respective electron capture detector for converting the explosives vapours content in said one path into matter incapable of producing a signal in the associated electron capture detector, said electron capture detectors each including means for emitting signals substantially similar to each other when said explosives vapours are absent from said atmosphere and signals detectably different from each other when said explosives vapours are present in said atmosphere, such that said difference in signals indicates the presence of said explosives vapours in said atmosphere.

6. An apparatus according to claim 4 in which the conversion means comprises a heater for maintaining said one path at a temperature to cause break-down of the explosive vapours into non-electron capturing components while leaving other expected electron capturing materials unaffected.

7. An apparatus according to claim 6 in which each flow path includes a membrane selectively permeable to constituents in the atmosphere capable of detection in the associated electron capture detector and a carrier gas supply for conveying the constituents passing through the membrane into the associated electron capture detector.

8. An apparatus according to claim 4 including circuit means for automatically detecting the presence of said particular constituent in the sampled atmosphere, the circuit means comprising a first difference detector to receive the outputs from said respective two detectors and a display device for receiving the output of the first difference detector, converter means connected across the output from the first difference and an input to the first difference detector from one of the two detectors and operable to maintain a zero output to the display device by adjusting the amplitude of signals received by the first difference detector from said one of the two detectors, and a second difference detector for receiving the outputs from the respective first and second detectors, a slope detector to receive the output from the second difference detector and operable when said output achieves a value associated with the presence of the particular constituent to hold the converter means in a steady condition thereby to enable a difference signal produced at the first difference detector to be presented at the display device.

9. An apparatus according to claim 8 including a hold means connected between the slope detector and the converter means.

10. An apparatus according to claim 9 in which an amplifier is included in the input to the first difference detector from said one of the detectors, the converter means being operable to control the gain of said amplifier.

11. An apparatus according to claim 4 in which said first and second flow paths have inputs open to a common atmosphere and at the upstream ends thereof, said detectors thereof being at the downstream ends of said flow paths, said flow paths being free of means capable of extracting single constituents therefrom and capable of furnishing a continuous flow to each detector.

12. An apparatus according to claim 4 including first difference detecting means responsive to differences between the output signals of the two detectors for providing a difference output signal, means for adjusting the amplitude of the output signal of one said detector in a manner to normally maintain said difference output signal of said first difference detecting means at zero in the absence of said particular constituent in said sampled atmosphere despite drift in output of a said detector, and means reponsive to a rapid change in the output signal of a said detector occuring upon appearance of said particular constituent in said sample atmosphere for blocking further adjustment by said adjustment means.

* * * * *

UNITED STATES PATENT OFFICE
CERTIFICATE OF CORRECTION

Patent No. 3,997,297  Dated December 14, 1976

Inventor(s) Anthony Jenkins and Douglas W. Isgrove

It is certified that error appears in the above-identified patent and that said Letters Patent are hereby corrected as shown below:

Column 5, line 40; change "claim 4" to ---claim 5---.

Signed and Sealed this

Eighth Day of March 1977

[SEAL]

Attest:

RUTH C. MASON  
*Attesting Officer*

C. MARSHALL DANN  
*Commissioner of Patents and Trademarks*